United States Patent [19]

Sawa et al.

[11] Patent Number: 4,514,556
[45] Date of Patent: Apr. 30, 1985

[54] 4,4'-METHYLENE-BIS-(2-ETHYL-5-METHYL IMIDAZOLE) AND METHODS OF PRODUCING AND USING THE SAME

[75] Inventors: Natsuo Sawa, Kagawa; Toshihiro Suzuki, Saitama; Shinji Okazaki, Kagawa, all of Japan

[73] Assignee: Shikoku Chemicals Corporation, Japan

[21] Appl. No.: 594,902

[22] Filed: Mar. 29, 1984

[30] Foreign Application Priority Data

Apr. 14, 1983 [JP] Japan .................... 58-66584

[51] Int. Cl.$^3$ ............ C08G 59/50; C08G 59/68; C07D 233/88
[52] U.S. Cl. .................... 528/117; 252/182; 528/94; 528/361; 528/407
[58] Field of Search ......... 528/94, 117, 361, 407; 548/336; 252/182

[56] References Cited

U.S. PATENT DOCUMENTS 3,507,831  4/1970  Avis et al. .................... 528/94
3,756,984  9/1973  Klaren et al. ................ 528/94
4,041,007  8/1977  Waters ....................... 528/117 X
4,417,010  11/1983  Shimp ........................ 528/94 X Primary Examiner—Earl A. Nielsen
Attorney, Agent, or Firm—Steele, Gould & Fried

[57] ABSTRACT

The disclosure relates to a novel compound 4,4'-methylene-bis-(2-ethyl-5-methyl imidazole) represented by the structural formula

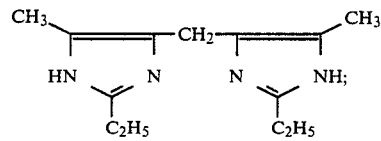

A method is provided for producing the novel compound subjecting formaldehyde or a methylenizing agent to thermal reaction with 2-ethyl-4-methyl imidazole in the presence of a catalyst; and a method of curing an epoxy compound and a method of accelerating curing the epoxy compound and a method of inhibiting crystallization of 2-ethyl-4-methyl imidazole, respectively by use of the new compound.

13 Claims, No Drawings

4,4'-METHYLENE-BIS-(2-ETHYL-5-METHYL IMIDAZOLE) AND METHODS OF PRODUCING AND USING THE SAME

BACKGROUND OF THE INVENTION

1. Field of the Invention

This invention relates to 4,4'-methylene-bis-(2-ethyl-5-methyl imidazole), used effectively as a curing agent or a cure accelerating agent of an epoxy compound or a crystallization retarder of 2-ethyl-4-methyl imidazole and to methods of producing and using the same.

2. Prior Art

Since epoxy resins are generally excellent in electrical insulation, mechanical strength, and resistance to chemicals, they are widely used in various industrial fields, and as curing agents, various curing agents are used such as fatty polyamine, aromatic polyamine, amine salt, tetraammonium salt, dicyanodiamide, urea, melamine, polycarboxylic acid, polycarboxylic acid anhydride, polyvalent phenol containing added condensate of phenols and aldehydes, polycarboxylic acid hydrazide, 2-ethyl-4-methyl imidazole.

Of the curing agents mentioned above, 2-ethyl-4-methyl imidazole (hereinafter referred to as "2E4MZ") is by nature a normal temperature crystallizable substance having a melting point of about 45° C. but 2E4MZ obtained immediately after having been refined by distillation under reduced pressure provides a liquid state for a considerably long time at normal temperature due to a supercooling phenomenon. Such liquid 2E4MZ is excellent in its compatibility with epoxy resin, it is highly valued as a curing agent or cure accelerator for the epoxy resin and is used today on a worldwide basis.

But this liquid 2E4MZ develops crystalline nuclei when the supercooling phenomenon is broken and rapidly solidifies in its entirety by the growth of crystals. When 2E4MZ solidifies in this manner, it is reduced in compatibility with epoxy resin, so that users tend to shun 2E4MZ liable to crystallize. The difficulty or ease with which 2E4MZ crystallizes depends upon the purity of 2E4MZ. Generally the higher in purity it is, the more easily it crystallizes and the lower in purity, the less liable it is to crystallize. However, it is difficult to find an ideal product high in purity and yet without atendency to crystallize from products of 2E4MZ commercially obtainable.

The present inventors have become confident during their course of research on 2E4MZ that compounds related to 2E4MZ must also be effective for use as curing agents or accelerators for epoxy resin, and have set about developing a new compound related to 2E4MZ.

Various compounds are thought to be related with 2E4MZ, and on the presumption that compounds most akin in property to 2E4MZ will be bis-compounds having 2E4MZ of two molecules bonded with an alkylene group, the inventors have attempted to synthesize the bis-compounds. But it is not an easy task to synthesize the compounds and after repeated failures, we have finally succeeded in synthesizing desired bis-compounds with good yield by heating 2E4MZ and formaldehyde or a methylenizing agent in the presence of a catalyst. The inventors have found that the 4,4'-methylene-bis-(2-ethyl-5-methyl imidazole) synthesized in this manner is effective for use as a curing agent or a cure accelerator for epoxy resin and, in addition, it is highly effective also for use as a crystallization inhibiting agent and have worked out the present invention.

SUMMARY OF THE INVENTION

Accordingly, a primary object of the invention is to provide a compound of 4,4'-methylene-bis-(2-ethyl-5-methyl imidazole) (hereinafter referred to simply as "bis-compound").

Another object of the invention is to provide a production method of efficiently synthesizing the bis compound.

Still another object of the invention is to provide a method of curing an epoxy compound using the bis-compound.

A further object of the invention is to provide a method of accelerating curing of an epoxy compound using the bis-compound.

A still further object of the invention is to provide a method of retarding crystallization of 2E4MZ using the bis-compound.

The first and second objects of the invention described above have been achieved by subjecting 2E4MZ and formaldehyde or a methylenizing agent to heat and reaction in the presence of a catalyst, the third object of the invention has been achieved by mixing a bis-compound into an epoxy compound having more than one epoxy base on an average in one molecule and heating the resulting compound, the fourth object has been achieved by mixing a bis-compound and a curing agent into the epoxy compound and heating the resulting compound, and the fifth object has been achieved by compounding a bis-compound into 2E4MZ.

Preferred embodiments of the invention will now be described in detail.

DETAILED DESCRIPTION OF THE PREFERRED EMBODIMENTS

The bis-compound is a new imidazole compound represented by the structural formula

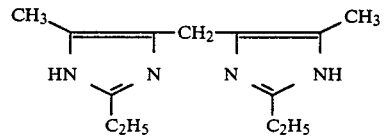

The properties of the compound are as follows:

Melting point: 260.5° C. (which involves sublimation)
Colorless crystal, basic, soluble in alcohol, insoluble in water, and hard of solution in acetone and toluene.

TLC (silica EtOH): Rf 0.05–0.35 (B.T.B. coloring)
$\nu_{KBr}^{cm-1}$: 2980, 1618 (fourth absorption), 1533, 1455 (first absorption), 1435 (second absorption), 1372, 1330, 1280, 1242, 1205, 1145, 1110, 1072 (third absorption), 1049 (5th absorption), 985, 967, 920, 880, 822, 788, 697

NMR (CD$_3$OD): $\delta$3.68, s, 2H (methylene); 2.61, q, 4H (methylene of ethyl base); 2.00, s, 6H (methyl); 1.21, t, 6H (methyl of ethyl base)

Mass (m/e): 232 (M+), 217 (M+-methyl), 203 (217-methylene), 123 (2E4MZ-H+methylene), 110 (2E4MZ)

Since this bis-compound has a structure common to 2E4MZ, it can produce substantially the same curing effect or cure accelerating effect as 2E4MZ on the epoxy compound, as will later be described, and when the bis-compound is compounded into 2E4MZ, it is presumed that the 2E4MZ produces association.

When 2E4MZ and formaldehyde or a methylenizing agent are heated together with a catalyst with or without the use of a solvent, the bis-compound described above is synthesized in the following manner.

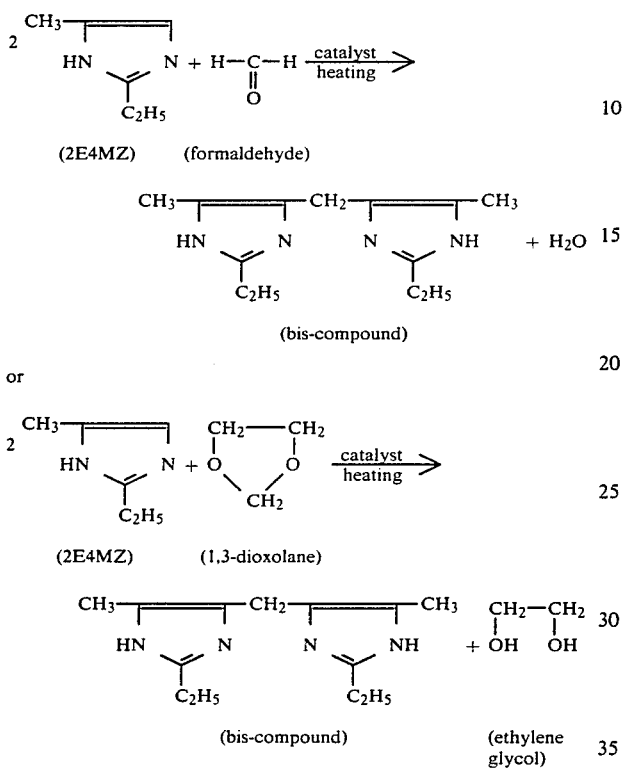

Referring more concretely to this synthesizing method, first a suitable mole ratio of 2E4MZ, formaldehyde (or methylenizing agent) and a catalyst are heated and stirred under normal pressure for a suitable period of time with or without the use of a suitable amount of solvent in a container having a tube filled with soda lime to cut off carbon dioxide in the open air Use of the tube is necessary when the catalyst is an alkali, but not when the catalyst is an alkali carbonate. By doing so, crystals soon come to be precipitated from a uniform solution. After the stirring is continued while heating for a further suitable period of time to thereby complete reaction, the reaction system is cooled to form crystals which are then filtered off. The filtered-off crystals (called first crystals) are once dissolved into an acidic aqueous solution, and crystals precipitated when the solution is alkalized are filtered out, washed with water, and dried to obtain a refined product. On the other hand, the filtrate from which the first crystals are separated is subjected to distillation under reduced pressure to collect unreacted 2E4MZ. Water-insoluble crystals in the distillation residue are filtered out (called second crystals). When the second crystals are treated in the same manner as the first crystals, purified product is likewise obtained. Of course, it is possible to purify the first and second crystals in accordance with an ordinary process (for example, rebonding or sublimation under reduced pressure).

The starting material 2E4MZ used in this invention is a material synthesized from propylene diamine and propiononitrile in accordance with Japanese patent publications No. 24965/1964, No. 1548/1967 and No. 151711/1966.

An aqueous solution of commercial Formalin serves the purpose for use as a formaldehyde adapted to be used in synthesizing the bis-compound of the invention. Paraform or 1,3-dioxolane-2, hexamethylenetetramine, Rongalite ® and condensation products formed from the reactions between formaldehyde and alcohols, etc. are used as a methylenizing agent. But the use of hexamethylenetetramine and Rongalite ® shows no advantage in yield over the use of formaline.

Water and alcohols such as methanol, ethanol, n-butanol, ethylene glycol are desirable for use as the solvent used in the method of production of the bis-compound of the invention. Under the catalyst are included lithium hydroxide, sodium hydroxide, potassium hydroxide, lithium carbonate, sodium amide, sodium carbonate, potassium carbonate, and Triton B ®. But sodium carbonate, potassium carbonate, and Triton B ® are inferior in property to the other catalysts mentioned above. The amount of catalyst used varies more or less depending upon the kind of catalyst, but generally speaking, the use of catalyst for 2E4MZ at a mole ratio of less than 0.2 answers the purpose and an amount more than that is not required. Reaction temperature varies depending upon the kind of solvent but a temperature of 70° to 130° C. is suitable. The synthesizing reaction in the invention sufficiently proceeds under normal pressure.

Of course, reaction may be effected under pressure. The acid used for preparing an acidic aqueous solution of crude intended materials (first and second crystals) is inorganic acid or organic acid such as hydrochloric acid, sulfuric acid, nitric acid, phosphoric acid, acetic acid, and formic acid. The group used for alkalizing an acidic aqueous solution having the crude intended materials dissolved therein is sodium hydroxide, potassium hydroxide, sodium carbonate, potassium carbonate, calcium hydroxide, calcium carbonate, ammonium, etc.

When the bis-compound is compounded into a polyepoxy compound having more than one epoxy group on an average in the molecule and the resulting compound is heated to a suitable temperature, the compound can be cured quickly and efficiently.

The epoxy compound used in this curing method may be

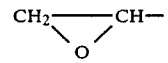

whose epoxy group is in molecular end position, or may be one which is generally called inner epoxide and which forms a group in the form of

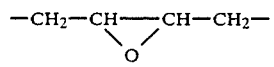

in the intermediate of molecular formula. This polyepoxy compound may be an aliphatic, cyclic-aliphatic, aromatic or heterocyclic compound, or may be substituted by a noninterfering substituent such as hydroxyl group, alkyl group, alkoxyl group, ester group, acetal group, and ether group.

The most desirable polyepoxy compound is polyglycydyl ether of polyvalent phenol such as bisphenol A, bisphenol F, resorcine, hydropuinone, bisphenol S, phenol formaldehyde resin, cresol formaldehyde resin.

To mention other suitable polyepoxy compounds, they are glycydyl ether of polyvalent alcohol such as (poly)ethylene glycol, (poly)propylene glycol, glycerine, trimethylol propane, 1,4-butandyol; polyglycydyl ester of polyvalent carboxylic acid such as phthalic acid, tetrahydrophthalic acid, hexahydrophthalic acid, methyl-endomethylenetetrahydrophthalic acid, adipinic acid, dimeric acid; glycydylamines derived from polyamine such as aniline, toluidine, 4,4′-diaminodiphenylmethane; epoxidated polyolefin such as vinyl cyclohexane oxide, 3,4-epoxy cyclohexyl-3,4-epoxy cyclohexane carboxylate, bis-(3,4-epoxy-6-methyl cyclohexylmethyl)adipate, epoxidated vegetable oil; and the like.

The ratio of suitable compound of bis-compound to a polyepoxy compound is 0.5 to 30 phr (part by weight per 100 parts by weight of polyepoxy compound), and a heating temperature is in the range of 60° to 240° C., preferably 100° to 180° C. One component system epoxy resin having a bis-compound compounded at the ratio mentioned above is less subject to change which brings about a reduction in working property as of increased viscosity over a long period of time in room temperature and is preserved in a stable state. When the resin is heated at the above temperature, it gets cured quickly and efficiently and becomes an excellent curing substance balanced in electric insulation, mechanical strength and resistance to chemicals.

Also, when the bis-compound of the invention is compounded as a cure accelerator or a co-curing agent into the above-mentioned epoxy compound with other curing agent and heated, it can accelerate curing of the epoxy compound.

In this cure acceleration method, an adequate amount of bis-compound compounded into a polyepoxy compound is in the range of 0.01 to 30 phr (part by weight per 100 parts by weight of polyepoxy compound) and preferably in the range of 0.05 to 10 phr. And the method is the same in heating temperature as the above-mentioned curing method.

Other curing agents are for example, aliphatic polyamine, aromatic polyamine, amine salt, tetraammonium salt, dicyanodiamide, urea, melamine, polycarboxylic acid, carboxylic acidanhydride, polyvalent phenol containing added condensate of phenols and aldehydes, hydrazide carboxylate, imidazole compound, etc.

Also in both cases of the curing method and curing acceleration method, a coloring pigment, an extender, a plasticizer and a reactive diluent of monoepoxy compound such as butyl glycydyl ether, phenyl glycydyl ether, or a solvent such as ketone type solvent, glycol type solvent, or aromatic petroleum naphtha may be added, if necessary.

As described, the bis-compound of the invention is extremely useful as a latent curing agent and a latent curing accelerator which do not exert a substantial influence upon preservative life or preservation stability of the system in which one component system epoxy resin, namely a polyepoxy compound is pre-mixed with a curing agent. Accordingly, epoxy resin type varnish, paint, adhesive agent, mold pouring material, dry lamination prepreg, forming compound, powdered paint, etc. capable of being cured within a short period of time at a temperature in the range of 60° to 240° C., preferably 100° to 180° C. can be formed by compounding the bis-compound singly or in combination with other curing agent, coloring pigment or the like into a polyepoxy compound.

Furthermore, this bis-compound is useful also as a crystallization inhibitor for 2E4MZ. It is worthy of special mention that compounding of the bis-compound into 2E4MZ can keep the 2E4MZ liquid over a long period of time.

In this manner, the reason why compounding of bis-compound into 2E4MZ maintains the supercooling phenomenon of 2E4MZ for a long time and keeps it liquid is theoretically not clear but may be presumed as follows.

Association of imidazoles unsubstituted at the 1 position is generally known and formation of hydrogen bond between hydrogen atoms of =N—H and tertiary nitrogen atoms is thought to be a cause of the association. The aspect of association is described below by way of example with reference to 2E4MZ wherein 2E4MZ is represented by

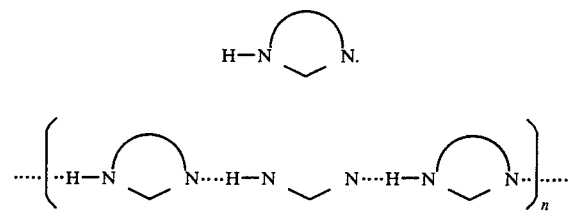

Although the molecular weight of 2E4MZ is as small as 110, the boiling point thereof is as high as 271° C. under atmospheric pressure and latent heat of evaporation is as high as 15,900 cal/mol. This fact is considered ascribable to association, one way or the other. Likewise, the supercooling phenomenon of 2E4MZ is considered due also to the association, and it becomes possible to hold the supercooling phenomenon of 2E4MZ for a long time by increasing the degree of association.

The bis-compound of the invention, as apparent from the above structural formula, has a structure common to 2E4MZ and has =N—H and tertiary nitrogen, each by twos, and each of which can relate by association. Accordingly, this bis-compound of the invention is thought to be bifunctional or quadrifunctional with respect to the association.

If the bis-compound of the invention is bifunctional and if the compound is mixed with 2E4MZ, the following linear association will result, wherein 2E4MZ is represented by

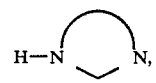

and the bis-compound of the invention is represented by

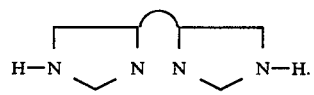

-continued

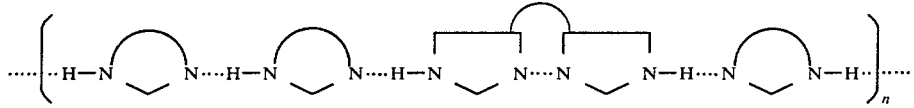

And if the bis-compound of the invention is quadrifunctional, the following linear bridged, namely reticular association will result.

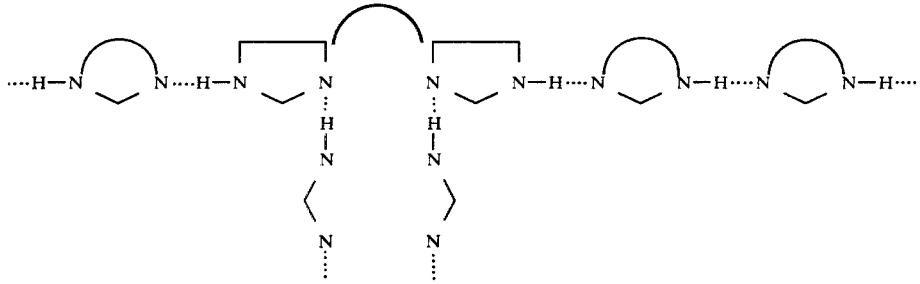

This concept cannot be demonstrated directly microscopically, but the reason why 2E4MZ remains liquid over a long time by compounding the bis-compound of the invention is presumed to be due to an increase in the degree of association by linear or reticular association.

Based upon the way of thinking described above, the amount of bis-compound mixed with 2E4MZ is allowed to be as small as is sufficient to increase association and, as will be verified by the results of embodiments to be later described, 2E4MZ provides a marked effect upon the inhibition of crystallization when a weight ratio of bis-compound to 2E4MZ is in the range of 0.1:99.9 to 3.0:97.0. This is due to the fact that when the amount of bis-compound of the invention compounded is smaller than the amount in the range described above, it becomes difficult to sufficiently increase the degree of association because of shortage in the bis-compound of the invention and on the other hand, when the amount of bis-compound exceeds the above range, the amount of the bis-compound which does not participate in association becomes excessive to thereby increase the action which inhibits association.

In this manner, the 2E4MZ having a small amount of bis-compound of the invention mixed thereinto is in reality reduced in purity, but since the bis-compound as aforestated has a structure common to the 2E4MZ and makes itself into an excellent curing agent or a cure accelerator, the 2E4MZ including bis-compound of the invention displays the same curing or cure accelerating property as high-purity 2E4MZ.

A description will now be given below of the invention with reference to examples in a more concrete form.

EXAMPLE 1

4.5 gm of commercial 37% formaline (a mole ratio of 0.75 to 2E4MZ), 9 gm of 2E4MZ, 0.25 gm of potassium hydroxide (KOH) (a mole ratio of 0.05 to 2E4MZ), and 27 ml of water were charged into a reactor having a magnetic stirrer, a reflux condenser, a thermometer, and a soda lime tube for interrupting carbon monoxide in the open air. The charge was heated while being stirred and a reaction temperature was held at about 102° C. for one and a half hours, and thereafter the system was cooled to filter off precipitated crystals. The crystals obtained were made into an acidic aqueous solution of hydrochloric acid, and the solution was sufficiently alkalized by potassium carbonate. The alkaline solution was filtered to obtain precipitated crystals, the crystals being washed and dreid to obtain 8.75 gm of intended product. The product was 92% in yield against 2E4MZ.

Incidentally, the 2E4MZ used in Example 1 and in those that follow is a relatively high purity product (made by Shikoku Chemicals Corporation) refined by distillation under reduced pressure and having a purity of 97% on an average and color tone of Gardner color standards Nos. 2 to 3 and it contains, when analyzed by gas chromatography, water, 2-ethyl-4-methyl imidazoline, 1-propyl-2-ethyl-4-methyl imidazole, 1-propyl-2-ethyl-5-methyl imidazole, 2,5-diethyl-4-methyl imidazole, and 2,4-diethyl-5-propyl imidazole in total amount of about 3% of impurities.

EXAMPLE 2

3.9 gm of commercial 37% formaline (a mole ratio of 0.65 to 2E4MZ), 9 gm of 2E4MZ, 0.25 gm of potassium hydroxide (a mole ratio of 0.05 to 2E4MZ), and 27 ml of water were subjected to reaction in the same manner as in Example 1. And the system was cooled to filter off precipitated crystals (first crystals) and the filtrate was subjected to distillation under reduced pressure to collect 0.6 gm of unreacted 2E4MZ distilled out. Water-insoluble matter (second crystals) out of the distillation residue was filtered off to be merged with the first crystals into an acidic aqueous solution of hydrochloric acid. The aqueous solution was alkalized by ammonium to filter off precipitated crystals. The crystals obtained were washed with hot water and dried to obtain 8.75 gm of intended substance (89% in yield against 2E4MZ and 93% in yield by correcting collected 2E4MZ (hereinafter referred to as correction yield).

EXAMPLE 3

3 gm of commercial 37% formaline (a mole ratio of 0.5), 9 gm of 2E4MZ (a mole ratio of 1.0), 2.25 gm of KOH (a mole ratio of 0.05) and 27 ml of water were treated in entirely the same manner as Example 2 to obtain 1.3 gm of 2E4MZ and 7.65 gm of intended substance (81% in yield and 94% in correction yield).

EXAMPLE 4

Entirely the same procedure as that in Example 2 was taken except that the formaline in Example 2 was used in an amount of 1.5 gm (mole ratio of 0.25) and hydrochloric acid was substituted by acetic acid, and 4.65 gm of 2E4MZ was collected and 3.4 gm of intended substance (36% in yield and 74% in correction yield) was obtained.

EXAMPLE 5

Entirely the same procedure as that in Example 3 was taken except that KOH was changed in amount from 0.25 to 0.13 gm (mole ratio of 0.025). Zero point seventy-five gm of 2E4MZ was collected and 7.1 gm of intended substance (65% in correction yield) was obtained.

EXAMPLE 6

Entirely the same procedure as that in Example 3 was taken except that KOH in Example 3 was changed in amount from 0.25 gm to 4.6 gm (mole ratio of 1.0), to obtain 2.3 gm of 2E4MZ and 4.65 gm of intended substance (65% in correction yield).

EXAMPLE 7

The same procedure as that in Example 3 was taken except that KOH was changed in amount from 0.25 gm to 0.13 gm (a mole ratio of 0.025) and simultaneously phosphoric acid was used instead of hydrochloric acid. One point zero five gm of 2E4MZ and 7.65 gm of intended substance (91% in correction yield) were obtained.

EXAMPLE 8

Entirely the same procedure as that in Example 3 was taken except that 0.25 gm of KOH in Example 3 was substituted by 0.3 gm of lithium hydroxide (LiOH) (mole ratio of 0.15). Zero point eighty-five gm of 2E4MZ and 7.5 gm of intended substance were obtained (87% in correction yield).

EXAMPLE 9

Entirely the same procedure as in Example 3 was taken except that 0.3 gm of LiOH in Example 8 was substituted by 0.5 gm of sodium hydroxide (NaOH) (mole ratio of 0.15). Zero point seven gm of 2E4MZ and 7.55 gm of intended substance (85% in correction yield) were obtained.

EXAMPLE 10

Entirely the same procedure as that in Example 8 was taken except that 0.3 gm of LiOH in Example 8 was substituted by 0.9 gm of lithium carbonate ($Li_2CO_3$) (mole ratio of 0.15) and simultaneously therewith hydrochloric acid was substituted by sulfuric acid and ammonium was substituted by NaOH. Two point nine gm of 2E4MZ and 6.5 gm of intended substance (69%) were obtained.

EXAMPLE 11

Entirely the same procedure as in Example 8 was taken except that 0.3 gm of LiOH in Example 8 was substituted by 0.7 gr. of KOH (mole ratio of 0.15) and water was substituted by 27 ml of methanol (but at a reaction temperature of 96° C.). Zero point sixty-five gm of 2E4MZ and 8.1 gm of intended substance (92% in correction yield) were obtained.

EXAMPLE 12

Entirely the same procedure as that in Example 8 was taken except that 0.3 gm of LiOH in Example 8 was substituted by 0.5 gm of NaOH (mole ratio of 0.15) and water was substituted by 27 ml of ethanol (but at a reaction temperature of 82° C.). Zero point three gm of 2E4MZ and 8.4 gm of intended substance (91% in correction yield) were obtained.

EXAMPLE 13

Nine gm of 2E4MZ (mole ratio of 1.0), 1.2 gm of paraform (mole ratio of 0.5) and 0.3 gm of KOH (mole ratio of 0.1) were charged into the same reactor as that in Example 1, reaction temperature of 128° C. was maintained for one and a half hours and thereafter the reaction mixture was subjected to distillation under reduced pressure to obtain 3.1 gm of 2E4MZ and 3.2 gm of intended substance (51% in correction yield).

EXAMPLE 14

Nine gm of 2E4MZ (mole ratio of 1.0), 1.2 gm of paraform (mole ratio of 0.5), 0.5 gm of KOH (mole ratio of 0.15) and 27 ml of ethylene glycol were allowed to react at 128° C. for one and a half hours. Ethylene glycol and 2E4MZ (0.5 gr.) were collected by distillation under reduced pressure. The distillation residue was dissolved in an aqueous solution of diluted nitric acid and the solution was alkalized by sodium carbonate to filter off precipitated crystals. The crystals were washed with water and dried to obtain 7.9 gm of intended substance (88% in correction yield).

EXAMPLE 15

Entirely the same procedure as that in Example 14 was taken except that ethylene glycol was substituted by n-butanol (but the reaction temperature was 116° C.). One point one gm of 2E4MZ and 7.7 gm of intended substance (91% in correction yield) were obtained.

EXAMPLE 16

Three gm of 2E4MZ (mole ratio of 1.0), 1 gm of 1,3-dioxylane-2 (mole ratio of 0.5 gm) and 0.1 gm of KOH (mole ratio of 0.15) were heated inside a closed tube at 300° C. for three hours. After the reaction, the closed tube was cooled and opened to filter off precipitated crystals. The crystals were dissolved in an acidic aqueous solution of hydrochloric acid, and the aqueous solution was alkalized by potassium carbonate to filter off precipitated crystals. The crystals were washed with water and dried to obtain 0.75 gm of intended substance (24% in yield).

EXAMPLES 17–19

To polyepoxy compound (trade name: Epicote 828 made by Yuka-Shell Epoxy Co., Ltd.) was added a specified amount of the bis-compound of the invention obtained in the aforestated examples and the mixture was passed through a three-roll machine so as to make the particles of a curing agent less than 5μ in grain size to obtain a uniform composition. Measurement was taken of the preservative stability, gelation time (curing property) of the composition thus obtained and a mold pouring material obtained by adding other filler to the composition and of the properties of the cured product. The results obtained are shown in Table 1 below.

Incidentally, compounding amount of the composition is shown in terms of weight unit, and the curing condition is heating at a temperature of 120° C. for one hour and at a temperature of 150° C. for four hours.

TABLE 1

| | Example 17 | Example 18 | Example 19 |
|---|---|---|---|
| Compounding: | | | |
| Epicote 828 | 100 | 100 | 100 |
| Bis-compound | 5 | 5 | 5 |
| Alumina | 0 | 200 | 0 |
| Silica | 0 | 0 | 200 |
| Total | 105 | 305 | 305 |
| Properties of composition: | | | |
| Outer appearance (visually) | milky white liquid | same as left | same as left |
| Specific gravity | 1.16 | 2.20 | 1.86 |
| Viscosity ($10^4$ cps/25° C.) | 2 | 260 | 450 |
| Gelation time (sec/150° C.) | 110 | 95 | 120 |
| Preservative stability (day/25° C.) | >60 | >60 | >60 |
| Properties of cured compositions: | | | |
| Outer appearance (visually) | Yellowish white, translucent | Grey white | same as left |
| Hardness (Shore D) | 88 | 95 | 95 |
| Thermal deformation temperature (°C.) | 155 | 163 | >300 |
| Bending strength (kg/mm$^2$) | 6.2 | 7.4 | 6.8 |
| Bending elasticity constant (kg/mm$^2$) | 305 | 1100 | 1410 |
| Dielectric constant (60Hz) | 3.4 | 5.2 | 3.6 |
| Dielectric loss tangent ($\times 10^{-3}$, 60Hz) | 2.8 | 4.3 | 2.2 |
| Dielectric breakdown voltage (kv/mm) | 20 | >20 | >20 |
| Volumetric resistivity (Ω-cm) | >$10^{15}$ | >$10^{15}$ | >$10^{15}$ |
| Volumetric resistivity after boiling (Ω-cm) | >$10^{14}$ | >$10^{14}$ | >$10^{14}$ |
| Water absorptivity (%/one hr. boil) | 0.3 | 0.1 | 0.1 |

By the way, the end point of the preservative stability is in the point of time at which the composition is stored at a temperature of 25° C. and the viscosity obtained from measurement of viscosity changes has amounted to twice as high as initial viscosity. The gelation time is found by a period of time measured in the manner that about 0.7 gm of sample is placed on a heating plate precontrolled to 150±0.5° C. and that the sample is spread over the plate by a stainless steel spatula to a size of about 20×30 mm$^2$ and is uniformly pressed down to the plate and kneaded, by operating the spatula at a speed of one reciprocation for about two seconds, until the composition ceases to rope between the spatura and the sample when the spatula is sometimes raised from the sample.

EXAMPLE 20

Seventy parts of polyepoxy compound A (trade name: Epicote 828 made by Yuka-Shell Epoxy Co., Ltd.), 30 parts of polyepoxy compound B (trade name: Epicote 834 do.), 2 parts of thixotroping agents (trade name: Bentone 38 made by NL Industries Co., Ltd.), 30 parts of extender (trade name: Talc P made by Takehara Chemical Industries Co., Ltd.), 6 parts of dicyanodiamide (made by Nippon Carbide Industries Co., Ltd.) and one part of bis-compound of the invention were kneaded uniformly by a three-roll machine, to obtain an adhesive composition. The composition, as shown below, continued in preservative property for more than two months at room temperature, cured quickly by heat treatment of higher than 120° C. and showed strong adhesion.

| | | |
|---|---|---|
| Preservative stability: | day/25° C. | >60 |
| Gelation time: | min/120° C. | 6.4 |
| | min/150° C. | 1.8 |
| | min/180° C. | 0.7 |
| Adhesive strength in shear: kg/mm | curing condition 0.5 hr/150° C. | |
| Copper to copper /20° C. | | 236 |
| Al to Al /20° C. | | 93 |
| Volumetric resistivity: Ω-cm/20° C. | | >$10^{15}$ |
| Dielectric breakdown voltage: kv/mm | | >20 |

EXAMPLES 21–22

The examples relate to those of powdered paint in which the bis-compound of the invention is singly used as a curing agent and is used as a cure accelerator together with a curing agent (acid anhydride).

The compositions shown in Table 2 below are sufficiently melted and kneaded by a two-roll machine preheated to a temperature of 85° to 95° C. The composition obtained were quickly cooled, pulverized and classified to obtain fluid immersion powdered paint filtered from mesh in the range of 80 to 270. The paint is useful for coating a film resistor, varistor, condenser, ceramic parts such as hybrid IC. The curing condition of the paint requires heating of the resin for one hour at a temperature of 150° C.

TABLE 2

| Compounding: | | |
|---|---|---|
| Epikote 1001 (remark 1) | 60 | 0 |
| Epikote 1004 (remark 1) | 40 | 100 |
| SH-6018 (remark 2) | 0.5 | 0.5 |
| Bis-compound | 5 | 0.5 |
| Anhydrous trimelitic acid | 0 | 8 |
| Silica powder (remark 3) | 50 | 80 |
| Iron oxide (remark 4) | 2 | 2 |
| Total | 157.5 | 191 |
| Physical properties: | | |
| Outer appearance (visually) | Rouge colored powder | same as left |
| Gelation time, min/150° C. | 1.5 | 3.5 |
| Specific gravity | 1.5 | 1.8 |
| Thermal deformation temperature (°C.) | 98 | 115 |
| Corner covering capacity (%) | 38 | 45 |
| Volumetric resistivity (Ω-cm) | $10^{15}$ | $10^{15}$ |
| Dielectric breakdown voltage (kv/mm) | 20 | 20 |
| Dielectric constant (60Hz/25° C.) | 3.8 | 3.2 |
| Dielectric loss tangent ($\times 10^{-3}$, 60Hz/25° C.) | 4.5 | 2.1 |

Remark 1: Polyepoxy compound made by Yuka-Shell Epoxy Co., Ltd.
Remark 2: Flow modifier made by Toray Silicone Co., Ltd.
Remark 3: Extender made by Tatsumori Co., Ltd. under trade name Crystallite
Remark 4: Coloring pigment made by Toda Kogyo Corp. under trade name of Red iron oxide R-100.

EXAMPLES 23–27

The bis-compound of the invention was mixed with 2E4MZ at a ratio indicated in Table 3 below to obtain five kinds of mixture. Thereafter, each mixture was stirred for a while at a temperature of 110° to 150° C. by interrupting flow of moisture from the open air to obtain a uniform liquid mixture. The mixture was left to cool and thereafter stored at 5° C.

In storing the mixture, the liquid mixture was sealed in an Erlenmeyer flask together with one iron cylinder 5 mm in diameter and 10 mm in length. The Erlenmeyer flask was stored at 5° C., and was rotated magnetically for a while once a day to accelerate precipitation of crystals. Crystallization took place by impetus of the turning cylinder, and when crystals were precipitated between the cylinder and the machine wall, the cylinder ceases to move magnetically.

A crystallization inhibiting effect was measured by variation in the number of days that passed before the cylinder ceases to rotate. The results of experiment conducted in the above procedure are shown in Table 3 below.

CONTRAST EXAMPLE 1

Measurement was taken of the number of days that passed before the cylinder ceased to move with respect to the exclusive use of 2E4MZ in the same procedure as in Examples 23–27. The results are also shown in Table 3.

TABLE 3

| Example No. | 2E4MZ (gm) | Bis-compound of the invention (gm) | Number of days that cylinder ceases to move (day) |
| --- | --- | --- | --- |
| 23 | 999 | 1 | 10 |
| 24 | 995 | 5 | 30 |
| 25 | 990 | 10 | 73 |
| 26 | 980 | 20 | 27 |
| 27 | 970 | 30 | 20 |
| Contrast Example 1 | 1000 | 0 | 3 |

It becomes apparent from Table 3 that mixing of a small amount of bis-compound with 2E4MZ produces a marked crystallization inhibition effect in comparison with the case where no bis-compound is mixed into 2E4MZ.

EXAMPLE 28

To 10 wt. parts of Epikote 828 (made by Yuka-Shell Epoxy Co., Ltd.) which is diglycydyl ether of bisphenol A was added three wt. parts of the mixture in Example 25 (consisting of 990 gm of 2E4MZ and 10 gm of bis-compound) and stirred well to obtain a uniform mixture A. For comparison, three wt. parts of 2E4MZ was likewise mixed to obtain a uniform mixture B. Gelation time and preservative stability of each mixture are as shown in Table 4 below.

TABLE 4

|  | Gelation time (150° C.) | Preservative stability (25° C.) |
| --- | --- | --- |
| Uniform mixture A | 1 min 10 secs | 9 hours |
| Uniform mixture B | 1 min 12 secs | 9 hours |

Preservative stability is shown in terms of time necessary before viscosity amounts to twice as high as properties of each mixture.

Characteristics of cured products obtained when each mixture was heat treated at 80° C. for four hours are shown in Table 5 below.

TABLE 5

| Item | Unit, condition | Uniform mixture A | Uniform mixture B |
| --- | --- | --- | --- |
| Glass transition point | °C. TMA process | 159 | 162 |
| Linear expansion coefficient | deg$^{-1}$ | $69 \times 10^{-6}$ | $72 \times 10^{-6}$ |
| Volumetric specific resistance | $\Omega \cdot$ cm 25° C. | $2 \times 10^{16}$ | $1 \times 10^{16}$ |
|  | $\Omega \cdot$ cm 150° C. | $3 \times 10^{13}$ | $2 \times 10^{13}$ |
| Dielectric constant | 1 KHz 25° C. | 3.25 | 3.26 |
|  | 1 KHz 150° C. | 3.54 | 3.56 |
| Dielectric loss tangent | % 1 KHz 25° C. | 0.91 | 0.92 |
|  | % 1 KHz 150° C. | 1.4 | 1.4 |
| Bending strength | kg/mm$^2$ 25° C. | 8.3 | 8.0 |
|  | kg/mm$^2$ 130° C. | 5.4 | 5.4 |
| Absorption factor by boiling | wt %, 4 hr. | 1.26 | 12.7 |

It is apparent from Tables 4 and 5 that there is no difference between uniform mixtures A and B. Accordingly, it follows that the mixture in Example 25 may be used in the same manner as 2E4MZ which is 97% in mean purity.

EXAMPLE 29

Comparison was made of cure accelerating effect of anhydride epoxy resinate between the mixture in Example 25 (consisting of 990 gr. of 2E4MZ and 10 gr. of bis-compound) and 2E4MZ. A composition of 100 wt. parts of Epikote 828, 100 wt. parts of acid anhydride by Dainippon Ink and Chemicals Inc. named Epiclon B-570 (made by Dainippon Ink and Chemicals Inc.) and 0.2 wt. parts of mixture in Example 25 is designated as A, and a composition having the mixture in Example 25 substituted exclusively by 2E4MZ is designated as B. The gelation time and thermal deformation temperature of compositions A and B are shown in Table 6 below.

TABLE 6

|  | A | B |
| --- | --- | --- |
| Gelation time (120° C.) | 25 min | 23.5 min |
| Thermal deformation temperature (°C.) | 129 | 129 |

Curing condition of cured products used in measuring thermal deformation temperature is 120° C./3 hrs.+150° C./4 hrs.

From the above, it follows that the mixture in Example 25 may be used in the same manner as 2E4MZ which is 97% in mean purity.

What is claimed is:

1. 4,4'-methylene-bis-(2-ethyl-5-methyl imidazole) represented by the structural formula $$\begin{array}{c} CH_3 \\ \phantom{X} \\ HN \end{array} \underset{C_2H_5}{\overset{}{\underset{N}{\bigvee}}} N - CH_2 - N \underset{C_2H_5}{\overset{CH_3}{\underset{N}{\bigvee}}} NH$$

2. A method of producing 4,4'-methylene-bis-(2-ethyl-5-methyl imidazole), comprising the step of subjecting at least one of formaldehyde and a methylenizing agent to thermal reaction with 2-ethyl-4-methyl imidazole in the presence of a catalyst.

3. The method of claim 2, wherein said methylenizing agent is selected from the group consisting of paraform and 1,3-dioxolane.

4. The method of claim 2, wherein said thermal reaction is made with the use of a solvent selected from the group consisting of water, methanol, ethanol, n-butanol, and ethylene-glycol.

5. The method of claim 2, wherein said catalyst is selected from the group consisting of sodium hydroxide, potassium hydroxide, sodium amide and lithium carbonate.

6. The method of claim 2, wherein said heating temperature is in the range of 20°–150° C.

7. The method of claim 2 wherein the mole ratio between 2-ethyl-4-methyl imidazole and at least one of formaldehyde and a methylenizing agent is in the range of 2:1 to 0.13:1.

8. A method of curing an epoxy compound, comprising the steps of: 4,4'-methylene-bis-(2-ethyl-5-methyl imidazole) with an epoxy compound having more than one epoxy group on an average in a molecule; and, heating the resulting mixture.

9. A method of accelerating curing of an epoxy compound, comprising the steps of: mixing 4,4'-methylene-bis-methyl imidazole with a curing agent into an epoxy resin to be cured, having more than one epoxy group on an average in a molecule; and, heating the resulting mixture.

10. A method of inhibiting crystallization of 2-ethyl-4-methyl imidazole, comprising the step of mixing 4,4'-methylene-bis-(2-ethyl-5-methyl imidazole) with 2-ethyl-4-methyl imidazole.

11. The method of claim 10, comprising the step of mixing the 4,4'-methylene-bis-(2-ethyl-5-methyl imidazole) and 2-ethyl-4-methyl imidazole by a weight ratio in the range of 0.1:99.9 to 3.0:97.0.

12. The method of claim 6, wherein said heating temperature is in the range of 70°–130° C.

13. The method of claim 7, wherein said mole ratio between 2-ethyl-4-methyl imidazole and at least one of formaldehyde and a methylenizing agent is in the range of 0.5:1.

* * * * *